United States Patent [19]

Smith

[11] Patent Number: 5,078,349
[45] Date of Patent: Jan. 7, 1992

[54] LOCKING MECHANISM FOR AN IV POLE

[75] Inventor: Arthur D. Smith, Greenville, Ohio

[73] Assignee: Midmark Corporation, Versailles, Ohio

[21] Appl. No.: 707,168

[22] Filed: May 24, 1991

Related U.S. Application Data

[63] Continuation-in-part of Ser. No. 509,128, Apr. 16, 1990, abandoned.

[51] Int. Cl.$^5$ .............................................. A47G 29/00
[52] U.S. Cl. .................................... 248/125; 248/412; 403/105; 403/109
[58] Field of Search .................. 248/188.5, 125, 200.1, 248/412; 403/104, 105, 109, DIG. 6

[56] References Cited

U.S. PATENT DOCUMENTS

| | | | |
|---|---|---|---|
| 2,010,292 | 8/1935 | Campbell | 155/94 |
| 2,010,306 | 8/1935 | Leech | 255/94 |
| 2,437,510 | 3/1948 | Ditty | 403/105 |
| 2,658,777 | 11/1953 | Rauglas | 287/58 |
| 4,037,839 | 7/1977 | Nelson | 273/84 |
| 4,113,222 | 9/1978 | Frinzel | 248/412 |
| 4,234,151 | 11/1980 | John et al. | 248/412 X |
| 4,318,526 | 3/1982 | Werner | 248/412 |
| 4,374,581 | 2/1983 | Karapita | 248/337 |
| 4,445,660 | 5/1984 | Karapita | 248/335 |
| 4,526,334 | 7/1985 | Rantakari | 248/157 |
| 4,662,771 | 5/1987 | Roe et al. | 403/108 |
| 4,695,021 | 9/1987 | Leinfelder | 248/168 |
| 4,712,830 | 12/1987 | Charbrol et al. | 297/42 |
| 4,757,778 | 7/1988 | Scaglia | 403/109 X |

FOREIGN PATENT DOCUMENTS 2053934 8/1982 Fed. Rep. of Germany .
3326244 2/1985 Fed. Rep. of Germany .

Primary Examiner—J. Franklin Foss
Attorney, Agent, or Firm—Biebel & French

[57] ABSTRACT

An adjustable IV pole assembly is disclosed including an inner rod which is telescopingly received within an outer tube for adjustment of the pole height. A locking mechanism is located on a top end of the outer tube for locking the inner rod against downward movement. The locking mechanism includes an inwardly tapered surface located at an end of the outer tube and a release sleeve positioned between the inner rod and the tapered surface wherein the release sleeve carries a plurality of balls which may wedge between the tapered surface and the inner rod to lock the inner rod against movement. In addition, the release sleeve is provided with a flange portion which extends radially outwardly beyond the circumference of the outer tube and which may be manually engaged to release the locking mechanism and thereby allow the inner rod to move downwardly relative to the outer tube.

12 Claims, 3 Drawing Sheets

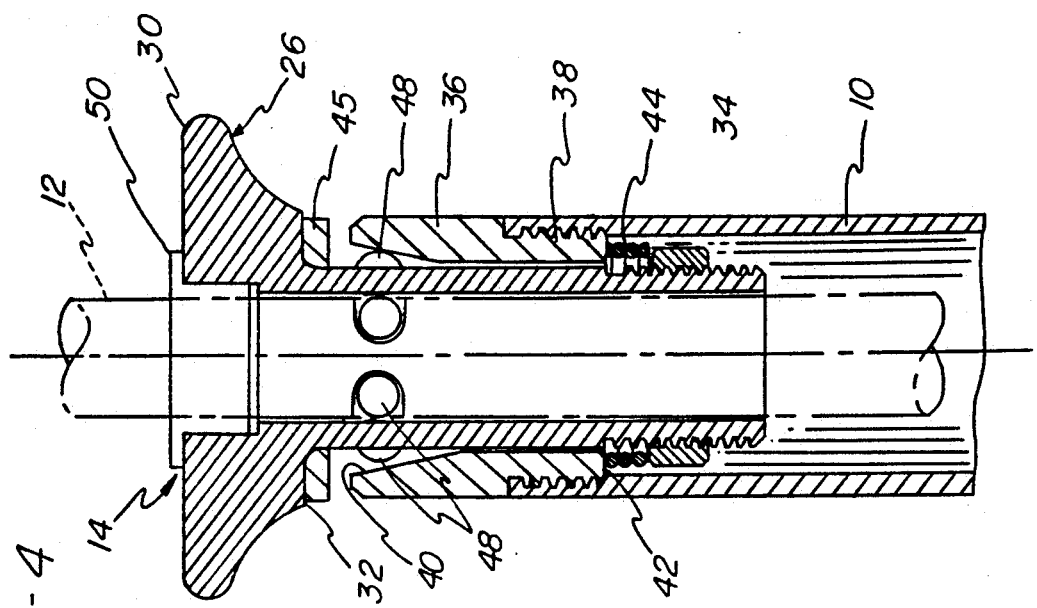
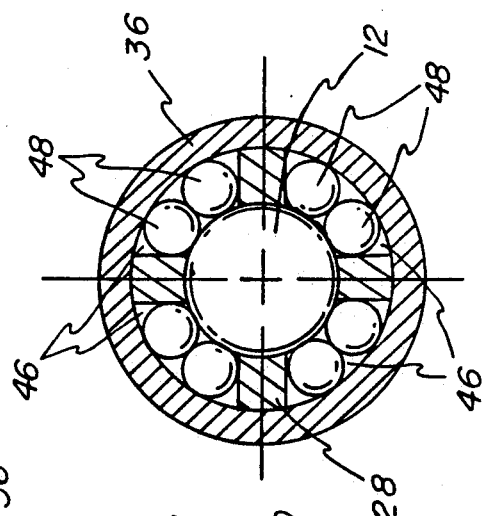
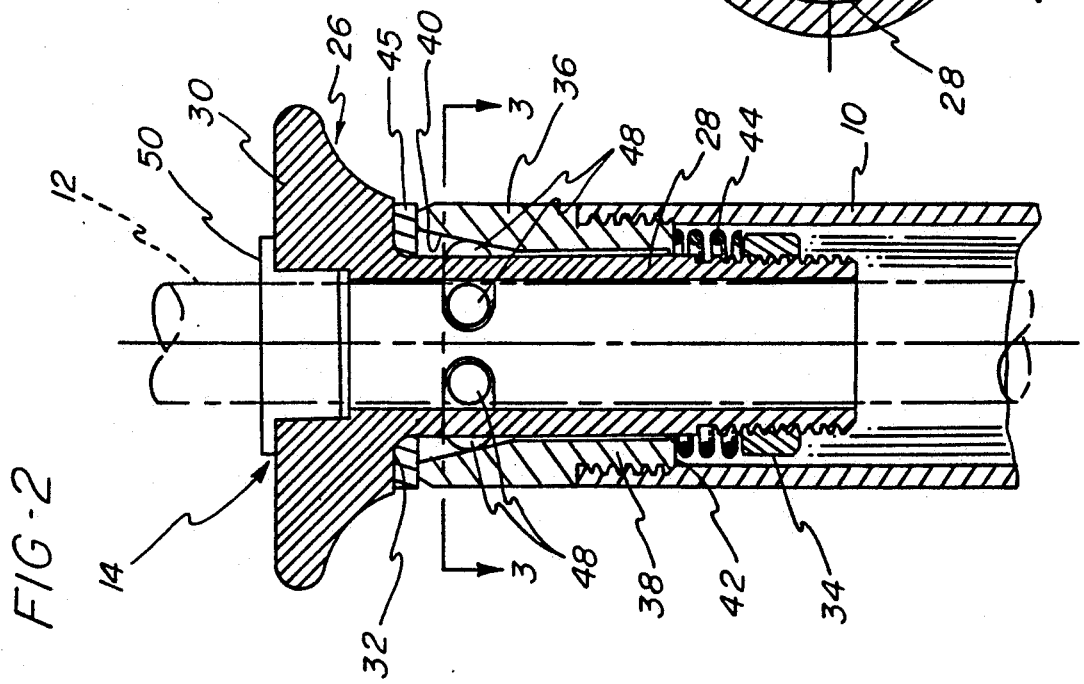

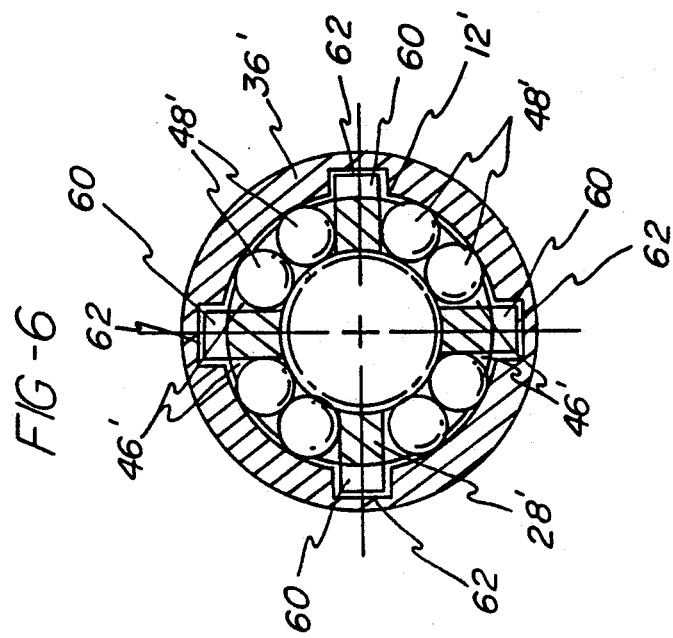
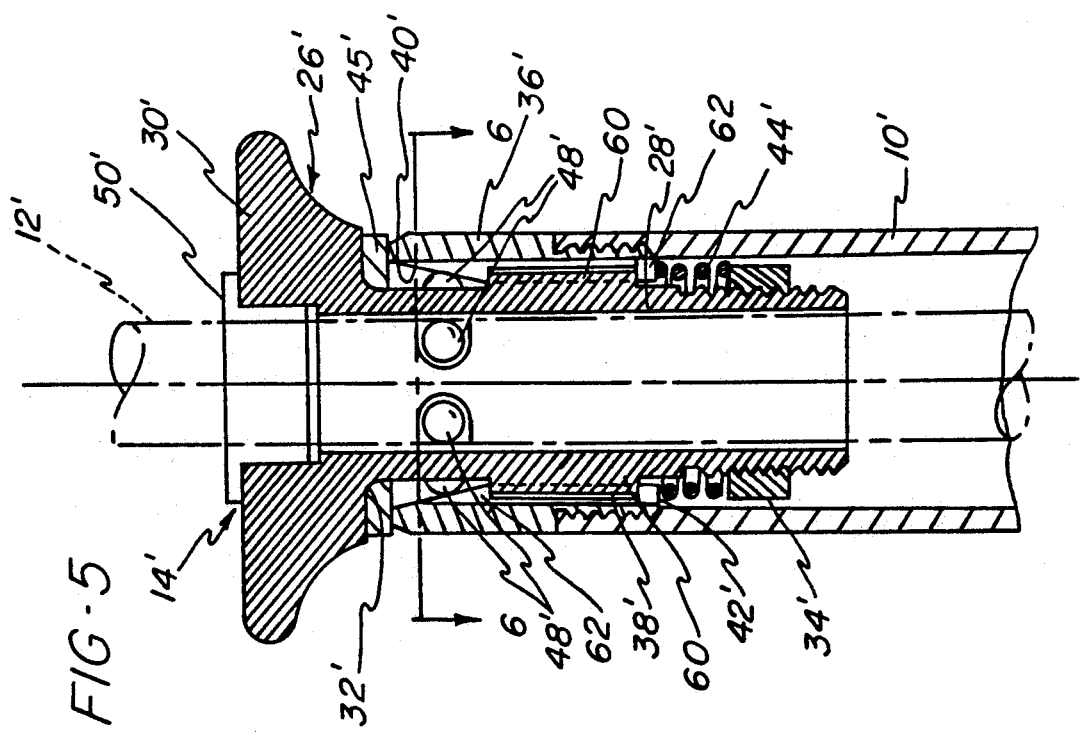

LOCKING MECHANISM FOR AN IV POLE

CROSS-REFERENCE TO RELATED APPLICATION

This application is a continuation-in-part of Ser. No. 507,128, filed Apr. 16, 1990 now abandoned.

BACKGROUND OF THE INVENTION

The present invention relates to a telescoping pole and, more particularly, to a telescoping pole for use in the intravenous administration of fluids.

Telescoping intravenous poles, or IV poles, are commonly used in hospitals for holding a container of IV fluid suspended above a patient. Such poles usually include an inner tube or rod which is longitudinally movable relative to an outer tube and which may be extended to the required height and then locked in place.

U.S. Pat. No. 4,113,222 to Frinzel and issued Sept. 12, 1978 discloses a typical IV pole in which a locking or clutch mechanism is carried at the lower end of a movable inner tube for engaging the interior surface of the outer tube to hold the pole at a desired height. Trigger bars located at the top of the pole may be manually engaged to disengage the clutch for movement of the inner tube when it is desired to change the height of the pole. Operation of this arrangement suffers from the problem that the hospital personnel manipulating the pole must often reach up above head level in order to manipulate the trigger levers for adjusting the pole. Further, the clutch of Frinzel is typical of current IV pole locking mechanisms in that it relies solely on a spring force to maintain the locking elements in engagement to prevent relative movement between the two tubes.

In addition, although the locking mechanism is only required for preventing downward movement of the pole, typical prior art IV poles require that the lock be released for both upward and downward movement and thereby hinder upward adjustment of the pole.

Consequently, there is a need for an IV pole which may be conveniently adjusted by hospital personnel and which firmly locks to prevent inadvertent downward movement of the IV container supporting portion of the pole.

SUMMARY OF THE INVENTION

The present invention provides an intravenous pole assembly for securely holding a container of intravenous fluid above a patient and for permitting easy access to hospital personnel for adjustment of the pole height.

The IV pole of the present invention includes an outer support tube which may be mounted in stationary relationship to a support member such as may be provided on a hospital bed. An inner rod having means for supporting an IV container is located within the outer tube and may be adjusted longitudinally relative to the outer tube.

A release sleeve is positioned over the inner rod and extends into the outer tube and includes a flange portion which extends radially beyond the outer circumference of the outer tube. The release sleeve includes means defining apertures therein for carrying a plurality of locking balls in contact with the inner rod.

A nut is positioned on an end of the outer tube and includes a locking surface which tapers inwardly toward the release sleeve and inner rod. The locking balls are carried for longitudinal movement by the release sleeve adjacent to the locking surface of the nut such that as the release sleeve is moved into the outer tube, the balls will be forced into engagement with the inner rod. A collar is located on the release sleeve at an end opposite from the flange portion and a compression spring is positioned between the collar and an end of the nut opposite from the locking surface for biasing the release sleeve into the outer tube such that the inner rod is locked from moving into the outer tube.

The flange portion of the release sleeve may be pushed away from the outer tube to release the locking mechanism and allow the inner rod to move downwardly into the outer tube. When the flange portion is released, the compression spring biases the release sleeve down into the outer tube to bring the balls into contact with both the inner rod and the locking surface and any downward force applied to the inner rod will further wedge the balls against the inner rod to thereby firmly lock the inner rod against downward movement.

In addition, when the inner rod is drawn upwardly, the balls will move upwardly slightly along the locking surface and away from locking engagement with the inner rod such that the inner rod is free to move upwardly.

Further, the release sleeve may be provided with radially outwardly extending splines for engaging in cooperating grooves formed in the inner surface of the nut. The splines and grooves prevent relative rotational movement between the sleeve and nut about the longitudinal axis of the IV pole. This in turn inhibits rotational movement of the inner rod relative to the outer tube.

Thus, the present invention provides a locking mechanism which is positioned on the outer tube at a convenient level for manipulation by hospital personnel. In addition, the IV pole assembly of the present invention provides means for positively locking the inner rod from movement into the outer tube and for permitting movement of the inner rod out of the outer tube without manual manipulation of the locking mechanism, as well as for inhibiting relative rotational movement between the inner rod and the outer tube.

Other objects and advantages of the invention will be apparent from the following description, the accompanying drawings and the appended claims.

BRIEF DESCRIPTION OF THE DRAWINGS

FIG. 2 is a cross-sectional view of the locking mechanism of the present invention in a locked position;

FIG. 3 is a cross-sectional view taken along line 3—3 in FIG. 2;

FIG. 4 is a cross-sectional view of the locking mechanism of the present invention in an unlocked position;

FIG. 5 is a cross-sectional view of a second embodiment of the present invention; and FIG. 6 is a cross-sectional view taken along line 6—6 in FIG. 5.

DETAILED DESCRIPTION OF THE PREFERRED EMBODIMENT

Figure 1:
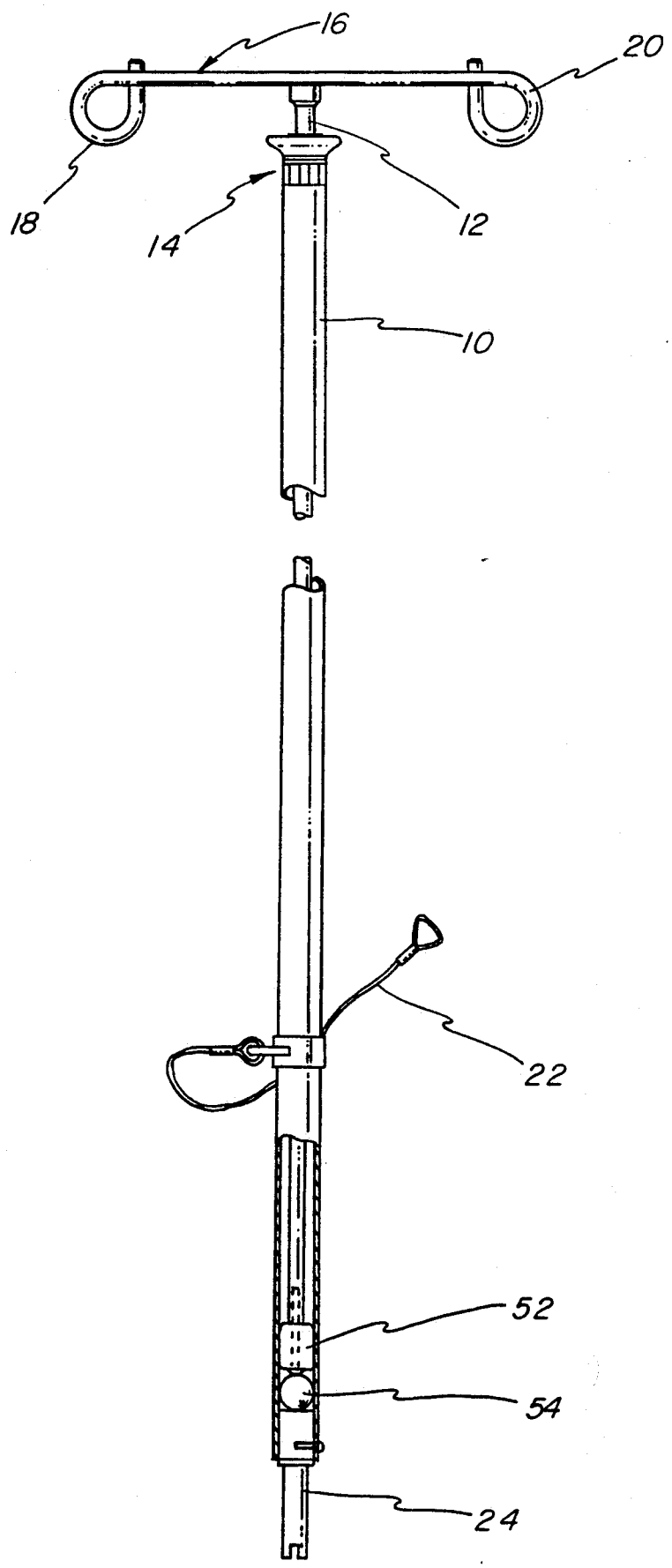
FIG. 1 is an elevational view of the locking pole assembly of the present invention with a lower portion thereof shown in partial cross-section.

Referring to FIG. 1, it can be seen that the intravenous pole assembly of the present invention includes an outer tube 10 and an inner rod 12 received within the outer tube 10. A locking mechanism 14 is positioned at an upper end of the outer tube 10 for engaging and locking the inner rod 12 against movement into the outer tube 10.

An IV container support bar 16 is rigidly mounted to an upper end of the inner rod 12 and includes a pair of retaining loops 18, 20 for supporting IV fluid containers such as bags or bottles from the pole on a stretcher or hospital bed.

The IV pole may be further provided with a cable assembly 22 attached to the outer tube 10 whereby the IV pole may be fastened to a stretcher to thereby prevent loss of the pole. In addition, a rod extension 24 may be attached to the outer tube 10 to engage a stretcher mounting bracket for supporting the IV pole on a stretcher or hospital bed.

Referring now to FIG. 2, the locking mechanism 14 of the present invention includes a release sleeve 26 which is formed as a substantially circular tubular member and which includes a shank portion 28 and a flange portion 30. The release sleeve 26 is positioned over the inner rod 12 and with the shank portion 28 extending into the outer tube 10. The flange portion 30 extends radially outwardly from the shank portion 28 and has an outer circumference which is greater than the outer circumference of the outer tube 10. A stop shoulder portion 32 is formed at the junction between the shank portion 28 and the flange portion 30 and forms a substantially planar surface extending around the shank portion 28 perpendicular to the longitudinal axis of the outer tube 10 and inner rod 12.

The release sleeve 26 further includes a collar 34 which is threadably engaged on the end of the shank portion 28 opposite from the flange portion 30. The collar 34 extends radially outwardly from the shank portion 28 and is formed with a diameter which is less than the inner diameter of the outer tube 10 such that the collar 34 may move longitudinally without contacting the outer tube 10.

A nut 36 is mounted to the upper end of the outer tube 10 and includes a threaded lower portion 38 extending into the outer tube 10 to engage a threaded portion on the interior surface thereof. The nut 36 further includes a first surface 40 which tapers inwardly toward the inner rod 12 to form a locking surface as will be described further below. In addition, a second surface 42 is formed on an end of the threaded portion 38 opposite from the first surface 40.

A compression spring 44 is positioned surrounding the shank portion 28 between the collar 34 and the second surface 42 of the nut 36 whereby the release sleeve 26 is biased downwardly into the outer tube 10. In addition, a washer 45 is located adjacent to the stop shoulder 32 between the flange portion 30 and the nut 36 to act as a cushion and seal between the flange portion 30 and the nut 36 when the release sleeve 26 is biased into the outer tube 10.

As may be seen in FIG. 3, the release sleeve 26 is formed with a plurality of apertures 46 and is preferably provided with four apertures 46 which are formed as elongated slots located circumferentially around the shank portion 28. A pair of locking balls 48 is positioned within each of the apertures 46 and the apertures 46 locate the balls 48 in engagement with the first surface 40 of the nut 36. The balls 48 are radially movable such that, as the release sleeve 26 moves into the outer tube 10, the balls 48 are forced inwardly by the first surface 40 into contact with the inner rod 12 to thereby lock the inner rod 12 against downward movement relative to the outer tube 10.

The locking mechanism 14 is constructed such that the release sleeve 26 has a maximum travel of approximately 1/16 inch whereby the locking mechanism may be easily manipulated by a person gripping the outer tube with his or her fingers and pushing upwardly on the flange portion 30 to release the inner rod 12 for downward movement.

The locking mechanism 14 is further provided with a flange bearing 50 which is positioned on a top surface of the flange portion 30 for closely surrounding the inner tube 12 as it moves through the release sleeve 26. The flange bearing 50 acts to clean the rod 12 of debris as it moves into the outer tube 10 and thus protects the locking mechanism 14 from becoming contaminated with any debris that may be attached to the pole 12.

As may be seen in FIG. 1, the lower end of the inner rod 12 is further provided with a stop member 52 which engages the lower end of the shank portion 28 to thereby prevent the lower end of the inner rod 12 from being extracted out of the outer tube 10 past the locking mechanism 14. In addition, an elastomer spring 54 in the form of a spher or ball is positioned between the rod extension 24 and the stop 52 to provide a cushioned stop for the inner rod 12 as it reaches the lower extent of its travel.

In operation, the inner rod may be adjusted upwardly relative to the outer tube 10 by pulling the rod 12 up through the locking mechanism 14. As the rod 12 is pulled upwardly, the balls 48 are caused to roll upwardly toward the wider portion of the tapered first surface 40 and away from the inner rod 12 such that they do not prevent movement of the rod 12. It should be noted that the spring 44 does not exert a great enough biasing force on the release sleeve 26 to cause the balls to lock the inner rod 12 against upward movement. Any attempt to move the rod 12 downwardly will result in the balls 48 moving downwardly toward the narrow portion of the tapered surface 40 such that the balls 48 wedge tightly against the surface of the inner rod 12 to prevent downward movement thereof. The diameter of the balls 48 and the taper of the first surface 40 are selected such that a large horizontal force component is produced by movement of the balls 48 downwardly into the narrow portion of the tapered first wall 40 whereby as the downward force applied to the inner rod 12 is increased, the force for locking the rod 12 against movement is also increased.

Referring to FIG. 4, it can be seen that when it is desired to move the rod 12 downwardly, the flange portion 30 may be manually engaged to move the release sleeve 26 upwardly such that the locking balls 48 are moved out of locking contact with the first wall 40 and the inner rod 12. When the inner rod 12 has moved down to the desired height, the flange portion 30 may be released to allow the release sleeve 26 to move downwardly and thus carry the balls 48 down into engagement with the first wall 40 and the inner rod 12 whereby the rod 12 may again be locked in place against further downward movement.

A second embodiment of the present invention is shown in FIGS. 5 and 6 in which elements corresponding to elements in the first embodiment are marked with the same numerals primed.

The locking mechanism 14' of the second embodiment includes all of the elements and operative characteristics of the embodiment of FIGS. 1–4, and additionally includes a plurality of splines 60 extending radially outwardly from the shank portion 28' of the release sleeve 26' for engagement in longitudinally extending grooves 62 formed in the inner surface of the nut 36'. The splines 60 and grooves 62 cooperate with each other to prevent rotation of the sleeve 26' relative to the nut 36'.

It is desirable to restrict the rotation of the sleeve 26' since, with the sleeve 26' free to rotate, the balls 48' locking the rod 12' in its longitudinal position may also rotate about a vertical axis as they move with the sleeve 26' which in turn corresponds to rotation of the rod 12' about its longitudinal axis. Thus, by preventing rotation of the sleeve 26', the balls 48' are no longer free to roll across the surface 40', and any rotation of the rod 12' relative to the outer tube 10 requires the rod 12' to move across the balls 48' in frictional sliding contact such that rotation of the rod 12' is restricted.

The construction of the second embodiment of the present invention particularly facilitates the use of the IV pole when an IV tube is extending from a fluid container supported on the support bar. By preventing rotation of the inner rod, the IV tube is prevented from being wrapped around the IV pole, which may occur when the inner rod is free to rotate.

As may be seen from the above description, the present invention provides a IV pole assembly having a locking mechanism which may be located at a convenient height for hospital personnel to use regardless of the height at which the upper portion of the inner rod is positioned. Further, the present invention allows the inner rod to be positioned upwardly to a desired height without requiring manipulation of the locking mechanism and therefore simplifies the adjustment operation.

In addition, the locking mechanism of the present IV pole assembly provides a positive means for locking the inner rod against vertical movement downwardly when in the locked position and provides a simple and easily manipulated mechanism for releasing the inner rod for downward movement.

While the forms of apparatus herein described constitute preferred embodiments of the invention, it is to be understood that the invention is not limited to these precise forms of apparatus and that changes may be made therein without departing from the scope of the invention which is defined in the appended claims.

What is claimed is:

1. An intravenous pole assembly comprising:
    an outer support tube;
    an inner adjustable rod located within said outer tube wherein said inner rod is longitudinally movable relative to said outer tube;
    a locking surface located at an end of said outer tube and tapering inwardly toward said inner rod;
    a release sleeve positioned between said inner rod and said locking surface and including a flange portion extending radially beyond said outer tube;
    means defining apertures in said release sleeve;
    locking elements positioned in said apertures and in engagement with said locking surface and being movable in a radial direction;
    means for biasing said release sleeve in a longitudinal direction into said outer tube whereby said locking elements are biased into engagement with said inner rod by said locking surface such that movement of said inner rod into said outer tube is prevented; and
    wherein said flange portion may be manually engaged and moved in a direction away from said outer tube to release said locking elements from said engagement such that said inner rod is free to move into said outer tube.

2. The assembly of claim 1 wherein said means for biasing comprises a compression spring.

3. The assembly of claim 1 wherein a nut is positioned in said end of said outer tube and said locking surface is formed in an interior surface of said nut.

4. The assembly of claim 3 wherein said means for biasing comprises a compression spring engaging an end of said nut.

5. The assembly of claim 4 wherein said release sleeve includes a radially extending collar located at an end of said release sleeve opposite from said flange portion and said spring engages said collar to bias said release sleeve into said outer tube.

6. The assembly of claim 1 wherein said locking elements comprise balls which are moved longitudinally along said locking surface by said means defining said apertures.

7. The assembly of claim 1 wherein said release sleeve includes a stop surface located between said flange portion and said outer tube to limit said longitudinal movement of said release sleeve into said outer tube.

8. The assembly of claim 1 wherein said release sleeve includes means defining four apertures and said locking elements comprise two balls located in each aperture.

9. The assembly of claim 1 including means for inhibiting relative rotation between said inner rod and said outer tube.

10. The assembly of claim 9 wherein said means for inhibiting rotation include cooperating surfaces formed on said release sleeve and said locking surface whereby relative rotation between said release sleeve and said locking surface is prevented.

11. The assembly of claim 10 wherein said cooperating surfaces comprise at least one spline formed on one of said release sleeve and said locking surface and at least one groove formed in the other of said release sleeve and said locking surface, said groove receiving said spline.

12. An intravenous pole assembly comprising:
    an outer support tube;
    an inner adjustable rod located within said outer tube wherein said inner rod is longitudinally movable relative to said outer tube;
    a nut positioned at an end of said outer tube and including a first surface which tapers inwardly toward said inner rod and a second surface located at an end of said nut opposite from said first end;
    a release sleeve extending through said nut and positioned between said inner rod and said outer tube and including a flange portion extending radially beyond said outer tube and a radially extending collar located at an end opposite from said flange portion and positioned within said outer tube;
    means defining four apertures in said release sleeve, said apertures having an elongated configuration in a circumferential direction around said release sleeve;
    a pair of locking balls positioned within each of said apertures and in engagement with said first surface, said balls being movable in a longitudinal direction with said release sleeve and being movable in a radial direction toward and away from said inner rod;

a compression spring surrounding a portion of said release sleeve and engaging said second surface of said nut and said radially extending collar to bias said release sleeve into said outer tube;

a stop surface formed on said release sleeve between said flange portion and said collar;

a washer for separating said stop surface from said nut as said release sleeve is biased into said outer tube by said spring whereby said stop surface cooperates with said washer and said nut to limit the longitudinal movement of said release sleeve; and wherein said longitudinal movement of said release sleeve into said outer tube causes said balls to be forced inwardly by said first surface into engagement with said inner rod to prevent movement of said inner rod into said outer tube and wherein said flange portion may be manually engaged to longitudinally move said release sleeve in a direction out of said outer tube such that said balls release said inner rod for movement into said outer tube.

* * * * *